United States Patent [19]
Levine

[11] Patent Number: 6,103,220
[45] Date of Patent: Aug. 15, 2000

[54] LYSINE DECARBOXYLASE INHIBITORS FOR THE PREVENTION AND TREATMENT OF PERIODONTAL DISEASE

[76] Inventor: Martin Levine, 505 Kensington Rd., Norman, Okla. 73072

[21] Appl. No.: 09/235,196

[22] Filed: Jan. 22, 1999

Related U.S. Application Data

[60] Provisional application No. 60/072,373, Jan. 23, 1998.

[51] Int. Cl.[7] .............................. A61K 7/16; A61K 7/22; A61K 31/195
[52] U.S. Cl. ................................. 424/54; 424/49
[58] Field of Search ................................................ 424/54

[56] References Cited

U.S. PATENT DOCUMENTS

| | | |
|---|---|---|
| 4,309,442 | 1/1982 | Bey et al. . |
| 4,330,559 | 5/1982 | Bey et al. . |
| 4,405,530 | 9/1983 | Gerhart . |
| 4,413,141 | 11/1983 | Bey et al. . |
| 4,438,270 | 3/1984 | Bey et al. . |
| 4,496,588 | 1/1985 | Bey et al. . |
| 4,560,795 | 12/1985 | Bey et al. . |
| 4,743,691 | 5/1988 | Bey et al. . |
| 4,866,206 | 9/1989 | Bey et al. . |
| 5,614,557 | 3/1997 | Bey et al. . |

FOREIGN PATENT DOCUMENTS

| | | |
|---|---|---|
| 868882 | 11/1978 | Belgium . |
| 881208 | 5/1980 | Belgium . |
| 881210 | 5/1980 | Belgium . |
| 881209 | 8/1986 | Belgium . |
| 46710 | 3/1982 | European Pat. Off. . |
| 2669629 A1 | 5/1992 | France . |

OTHER PUBLICATIONS

Hcaplus 117:239862 Morellend FR. Demone 2669629A1, May 1992.

Yarlett et al. Biochem. Pharmacol. 44(2): 243–250 Hcaplus 117:184322, 1992.

Poso et al. Biochem. Biophys. Res. Commun. 125(1): 205–210 Hcaplus 102:75483, 1984.

Bey et al J. Org. Chem. 44(15):2732–2742 Hcaplus 91 : 74865, 1979.

S. Offenbacher, "Periodontal Diseases: Pathogenesis," *Ann. Periodontl*, 1:821–878, 1996.

Haffajee et al., "Microbial Etiological Agents of Destructive Periodontal Diseases," *Periodontology 2000*, 5:78–111, 1994.

Haffajee et al., "The Effect of SRP on the clinical and Microbiological Parameters of Periodontal Diseases," *J. Clin Periodontol*, 24:324–334, 1997.

Socransky et al., "The predominant Cultivable Microbiota of Active and Inactive Lesions of Destructive Periodontal Diseases," *J. Clin Periodontal*, 15:316–323, 1988.

Haffajee et al., "Effect of Modified Widman Flap Surgery and Systemic Tetracycline on the Subgingival Microbiota of Periodontal Lesions," *J. Clin Periodontol*, 15:235–262, 1988.

Haffajee et al., "Clinical and Microbiological Features of Subjects with Adult Periodontitis Who responded Poorly to Scaling and Root Planing," *J. Clin Periodontol*, 24:767–776, 1997.

S. Ciancio, "Current Status of Indices of Gingivitis," *J. Clin Periodontol*, 13:375–378, 1986.

Loesche et al., "Bacteriology of Human Experimental Gingivitis: Effect of Plaque and Gingivitis Score," *Infection and Immunity*, 21(3):830–839, 1978.

(List continued on next page.)

*Primary Examiner*—Shep K. Rose
*Attorney, Agent, or Firm*—Dunlap, Coddings & Rogers, PC

[57] ABSTRACT

An agent, α-difluoromethyl lysine (DFML) or α-monofluoromethyl lysine (MFML), inhibits lysine decarboxylases produced by bacteria associated with periodontal tissues. Inhibition of such lysine decarboxylases can prophylactically and therapeutically treat periodontal diseases such as gingivitis and periodontitis. The agent may be incorporated into toothpastes, mouthwashes, irrigation solutions, tablets, periodontal treatment packs, or an adhesive paste or film coatings for applying to the teeth.

8 Claims, 6 Drawing Sheets

OTHER PUBLICATIONS

P.E. Kolenbrander, "Coaggregation of Human Oral Bacteria: Potential Role in the Accretion of Dental Plaque," *Journal of Applied Bacteriology Symposium Supplement*, 74:79S–86S, 1993.

Kolenbrander et al., "Coaggregation: Specific Adherence Among Human Oral Plaque Bacteria," *The FASEB Journal*, 7:406–413, Mar. 1993.

Moore et al., "Bacteriology of Experimental Gingivitis in Young Adult Humans," *Infection and Immunity*, 38(2):651–667, 1982.

Socransky et al., "Microbial Complexes in Subgingival Plaque," *J. Clin Periodontol*, 25:134–144, 1998.

Niederman et al., "Short–chain Carboxylic Acid Concentration in Human Gingival Crevicular Fluid," *J Dent Res*, 76(1):575–579, Jan. 1997.

Niederman et al., "Short–chain Carboxylic–Acid–Stimuated, PMN–Mediated Gingival Inflammation," *Crit Rev Oral Biol Med*, 8(3);269–290, 1997.

R. Williams, "Periodontal Disease", *The New England Journal of Medicine*, 332 (6):373–381, Feb. 1990.

J.I. Salonen, "Proliferative Potential of the Attached Cells of Human Junctional Epithelium," *J. Periodontol Res*, 29:41–45, 1994.

Griffiths et al., "Permeability of the Gingival Tissues To IgM During An Experimental Gingivitis Study in Man," *Archs Oral Biol.*, 42(2):129–136, 1997.

Schroeder et al., "Fine Structure of the Developing Epitelial Attachment of Human Teeth," In: *Monographs in Developmental Biology*, vol. 2, Edited by A. Wolsky, S. Karger AG, Basel Switzerland, 1977.

Overman et al., "Characterization of the Human Junctional Epithelial Cells Directly Attached to the Tooth (DAT Cells) in Periodontal Disease," *J. Dent Rese*, 73 (12):1818–1823, Dec. 1994.

Levine et al., "Effect of Dental Plaque Extracts on Mammalian Cells In Vitro," *J. Periodont Res* 8:296–303, 1973.

M. Levine, "The Role for Butyrate and Propionate in Mediating Hela–Cells Growth Inhibition By Human Dental Plaque Fluid From Adult Periodontal Disease," *Archs Oral Biol*, 30 (2):155–159, 1985.

Levine et al., "Characterization and Cross–Reactivity of Rabbit Antisera to Plaque Toxins," *Oral Microbiol Immunol*, 2:88–91, 1987.

Sabo et al., "Purification and Physical Properties of Inducible *Escherichia Coli* Lysine Decarboxylase," *Biochemistry*, 13 (4):662–670, 1974.

Holmes et al., "Unusual Gram–Negative Bacteria, Including Capnocytophaga, Eikenella, Pasteurella and Streptobacillus," In: *Manual of Clinical Microbiology*, Edited by P.R. Murray, ASM Publishing Washington, D.C., pp. 499–508, 1995.

Levine et al., "Lysine Decarboxylase—A New Virulence Factor in Gingivitis," *J. Dental Res*, 77(110) Abstract #39, 1998.

Janne et al., "Polyamines in Rapid Growth and Cancer," *Biochim. Biophys. Acta*, 473:241–293, 1978.

Finaly et al., "Common Themes in Microbial Pathogenicity," *Microbiological Reviews*, 53(2):210–230, Jun. 1989.

Simpson et al., "Killing of Human Myelomonocytic Leukemia and Lymphocytic Cell IInes by *Actinobacillus actinomycetemcomitans* Leukotoxin," *Infection and Immunity*, 56(5);1162–1166, May 1988.

Genco et al., Molecular Factors Influcencing Neutrophil Defects in Periodontal Disease, *J. Dent Res*, 65(12)1379–1391, Dec. 1986.

Lally et al., "Analysis of the *Actinobacillus actinomycetemcomitans* Leukotoxin Gene," *The Journal of Biological Chemistry*, 264(26):15451–15456, 1989.

McAnally et al., "Bacteria Reactive to Plaque–Toxin–Neutralizing Monoclonal Antibodies are Related to the Severity of Gingivitis at the Sampled Site," *Oral Microbiol Immunol*, 8:69–74, 1993.

Pegg et al., "Decarboxylation of Ornithine and Lysine in Rat Tissues," *Biochimica et Biophysica Acta*, 568:416–427, 1979.

Rudnic et al., "Tablet dosage forms," In: *Modern Pharmaceutics, Third edition revised and expanded*, Edited by Banker G.S. & Rhodes C.T., Marcel Dekker, Inc., NY., pp. 333–394, 1996.

Nairn J.G., "Solutions, emulsions, suspensions and extracts," In: *Remington's Pharmaceutical Sciences*, Edited by Hoover J.E., Mack Printing Co., Easton, PA., pp. 1519–1544 1999.

Ciancio et al., "Prophylaxis Pastes, Dentifrices, and Mouthwashes," In: *Clinical Pharmacology for Dental Professionals, Third Edition*, Year Book Medical Publishers Inc., Chicago, pp. 405–407, 1989.

Phan et al., "Spectrophotometric Assay for Lysine Decarbosylase," *Analytical Biochemistry*, 120:193–197, 1982.

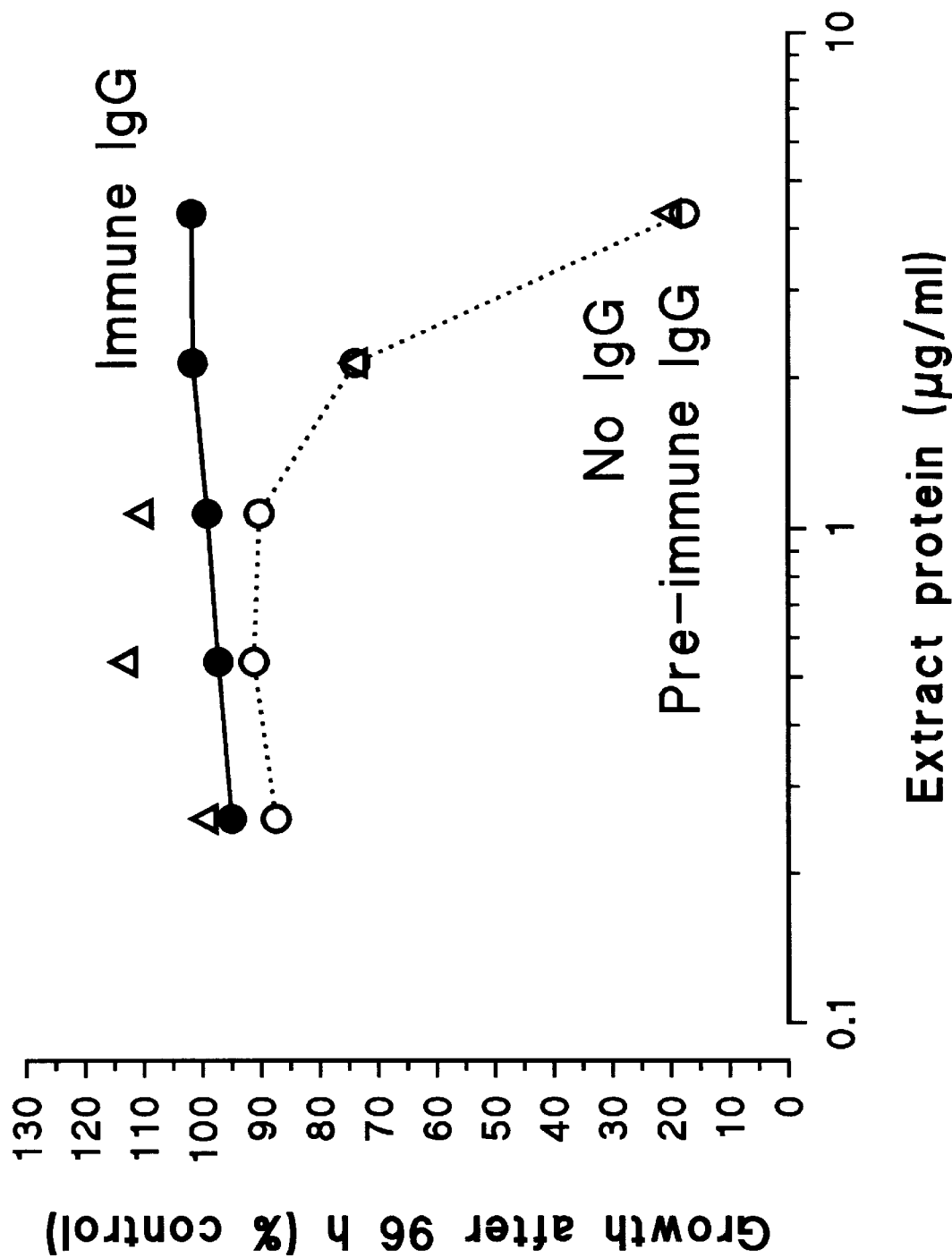

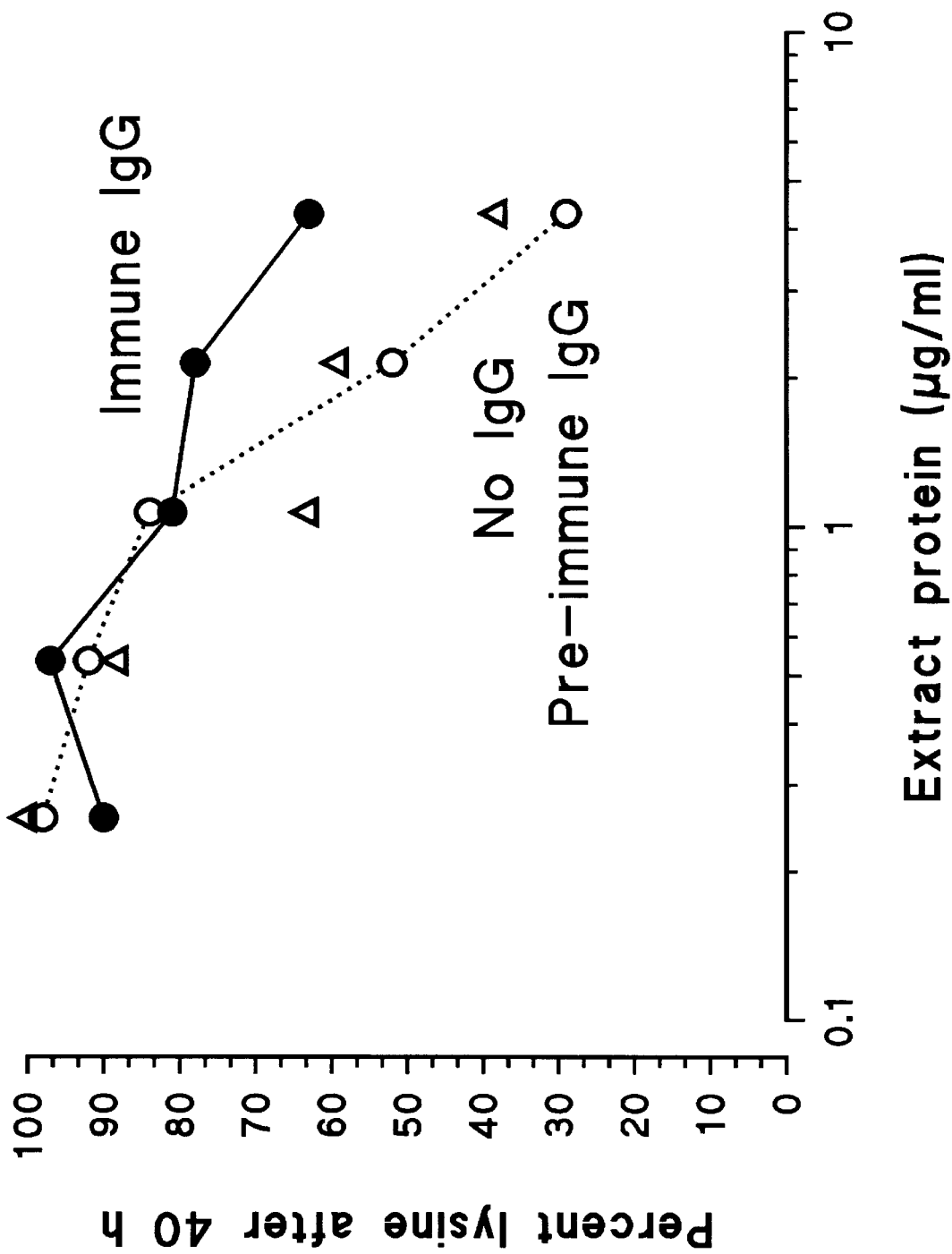

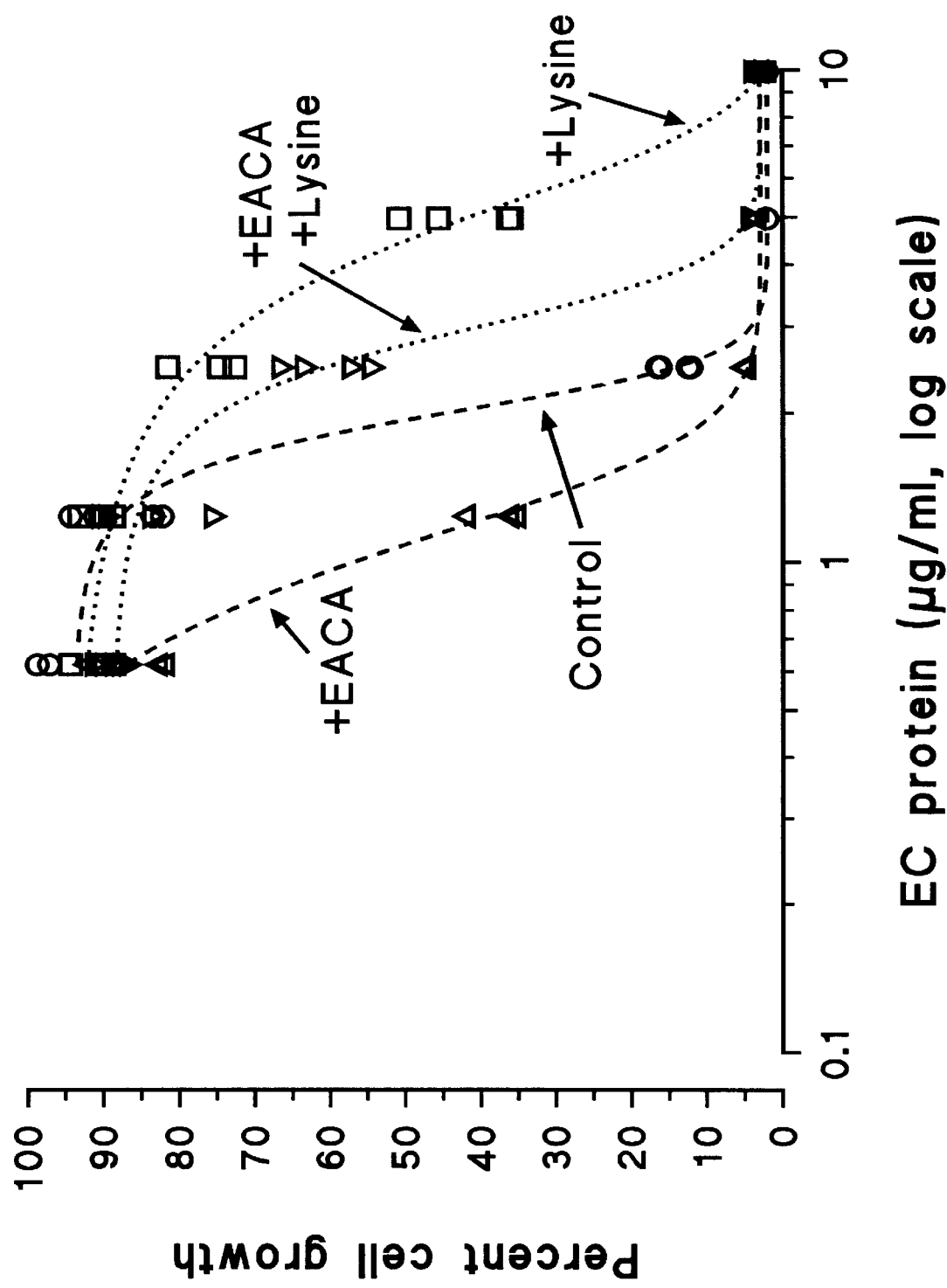

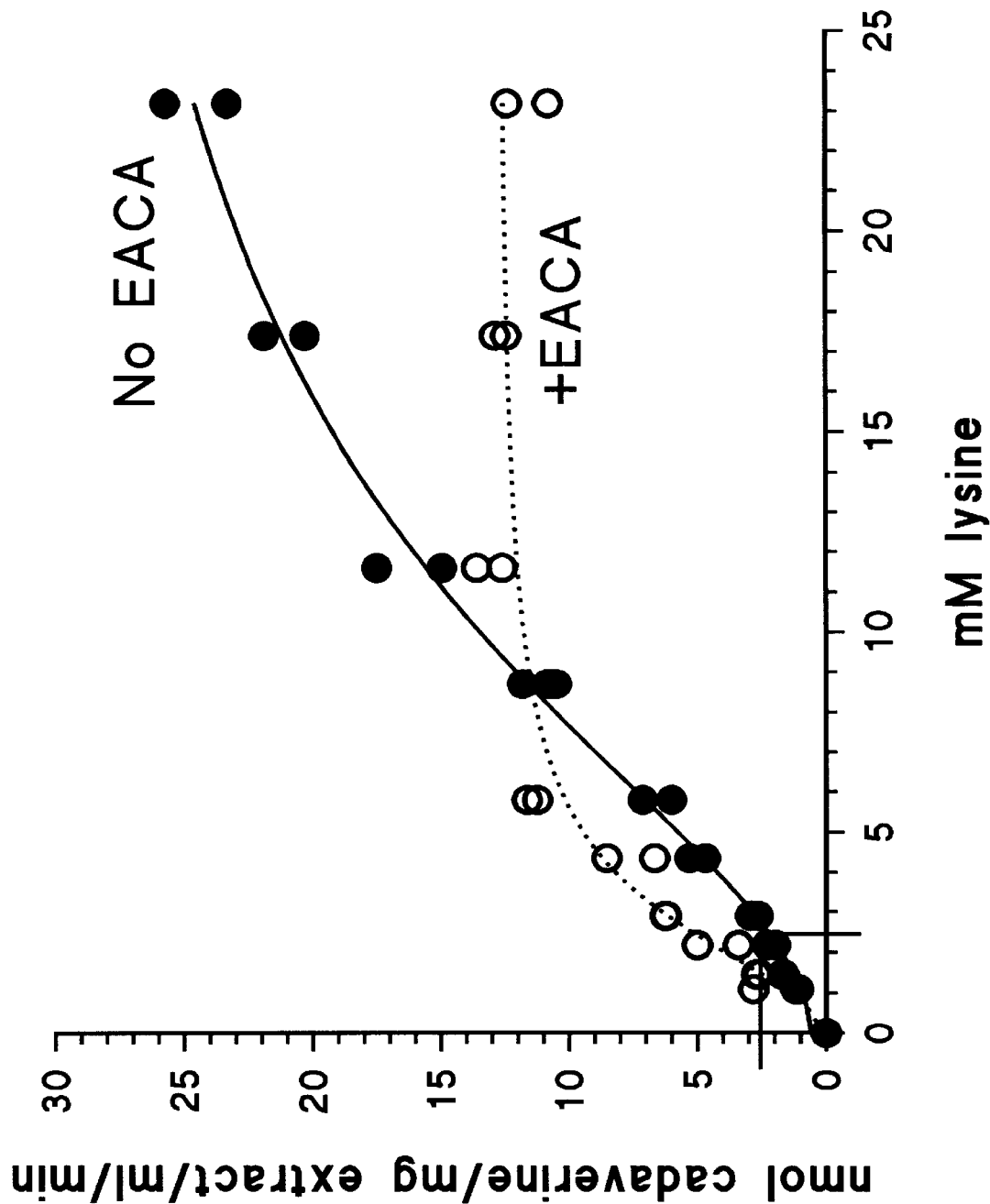

LYSINE DECARBOXYLASE INHIBITORS FOR THE PREVENTION AND TREATMENT OF PERIODONTAL DISEASE

CROSS REFERENCE TO RELATED APPLICATIONS

This application claims the benefit of U.S. Provisional Application Ser. No. 60/072,373, filed Jan. 23, 1998.

STATEMENT REGARDING FEDERALLY SPONSORED RESEARCH OR DEVELOPMENT

Not Applicable

BACKGROUND

Adult periodontal disease is a widespread medical problem that is difficult to treat, especially in the middle-aged and elderly. It develops when bacteria indigenous to the oral cavity colonize gingival sulci, forming bacterial plaques in the absence of oral hygiene. Inflammation (gingivitis) develops and eventually spreads, causing tooth attachment loss (periodontitis). The diversity of the oral flora, the chronic nature of the disease, and the absence of a generally accepted animal or in vitro model, have made the molecular pathogenesis of this disease by bacteria difficult to study [1]. Therapies for this disease have also been hampered by ignorance of the bacterial induction process [2]. Current therapy requires that the dentist improve oral hygiene by debridement (scaling and root-planing) and repair tissue architecture using periodontal surgery as necessary [3]. The patient must undertake regular toothbrushing and flossing [4,5]. This therapy is expensive, time-consuming and unpredictable in its outcome [6].

Gingivitis is detected when the gingival sulcus, a shallow crevice between the teeth and gingiva, bleeds on gentle probing [7]. Bacterial plaques extend into this sulcus by an orderly process of colonization and coaggregation in the absence of oral hygiene [8–10]. The initial plaque is mostly composed of actinomyces and viridans streptococci, but it is soon overgrown by Gram-negative bacteria and spirochetes [8,11]. One of the earliest bacterial complexes that overgrow the initial flora in gingival sulci consists of E. corrodens and Capnocytophaga spp. These Gram-negative bacteria are found equally in sulci that are both healthy and inflamed, whereas different bacterial complexes are found exclusively at inflamed sulci and in association with uncontrolled periodontitis [12]. Many of these disease-associated bacteria are thought to induce inflammation by making short-chain fatty acids that inhibit cell growth in culture [13,14]. A key observation is that the colonization by indigenous bacteria is required before the disease-associated flora appears in a sulcus. The number of inflamed sulci increases until, by 21 days of no oral hygiene, gingivitis is apparent throughout the mouth [11]. Eventually, the tooth attachment recedes beneath the cemental-enamel junction, forming periodontal pockets or causing gingival recession [15].

A gingival sulcus is formed where the oral epithelium meets the teeth. At the base of a sulcus, the oral epithelium differentiates into a junctional epithelium that mediates the epithelial attachment by further differentiating into dentally attached cells (DAT cells) at the enamel surface (FIG. 1A). The DAT cells are epithelial basal cells and undergo mitosis in vivo or when cultured in vitro [16]. A key observation is that the coronal DAT cells are distant from underlying capillaries (FIG. 1A) and grow on an interstitial fluid transudate across the base of healthy sulci [17]. The bacterial complexes lie about 0.5 mm above the most coronal DAT cells in a sulcus. In gingivitis, these cells disappear and the junctional epithelium becomes filled with neutrophilic granulocytes traversing from the underlying blood vessels (FIG. 1B) until it is no longer viable and periodontitis has developed [18,19]. The bacteria target the proliferative capacity of junctional epithelial DAT cells initially and the remainder of the epithelial attachment subsequently.

Saline extracts of bacterial plaques contain toxic proteins and short chain fatty acids that inhibit mammalian cell growth in culture [20–22]. The short chain fatty acid content indicates the presence of disease-associated bacteria in the samples. The toxic proteins were identified with plaque toxin-neutralizing monoclonal antibodies [23] and found to cross-react with a toxic 80 kilodalton protein (p80) from E. corrodens [24]. This protein is homologous to lysine decarboxylases from enteric bacteria [25], enzymes that metabolize extracellular lysine into cadaverine and carbon dioxide [26]. The inventor has found that this enzyme inhibits mammalian cell growth by depleting the culture medium of lysine, an amino acid which is not synthesized de novo by mammalian cells.

BRIEF DESCRIPTION OF THE DRAWINGS

FIG. 2A and 2B are graphs showing that IgG antibodies to the active site peptide prevents growth inhibition and loss of lysine. Immune IgG, ●—●. Pre-immune IgG, ○ . . . ○. No IgG Δ.

FIG. 3 is a graph showing how changes in the initial lysine concentration and enzyme activity affects growth inhibition. Percent inhibition of growth was graphed against amount of E. corrodens extract in the culture fluid. Control, 0.22 mM lysine, ○ . . . ○; 0.72 mM lysine □ . . . □; 0.42 mM EACA, Δ—Δ; and 0.72 mM lysine and 0.42 mM EACA, ▽ . . . ▽.

FIG. 4A and 4B are graphs showing cadaverine production as a function of initial lysine concentration in the presence and absence of 42 mM ε-amino-n-caproic acid (EACA). Although EACA inhibits lysine decarboxylase from E. coli [26], this graph shows that it activates this enzyme from E. corrodens extracts when the lysine concentrations are low like those in the culture media in the experiment shown in FIG. 3 (0.22–0.72 mM lysine). Initial rate of cadaverine produced (from 0.3 μg E. corrodens extract protein/ml) graphed against the initial lysine concentration. A. Cadaverine produced after 20 min: Enzyme only: ●—●; with 0.42 mM EACA ○ . . . ○. B. Enlarged inset, cadaverine produced after 16 h (limited substrate): Enzyme only ●—●; with 0.42 mM EACA ○ . . . ○.

DESCRIPTION OF THE INVENTION

Figure 1:
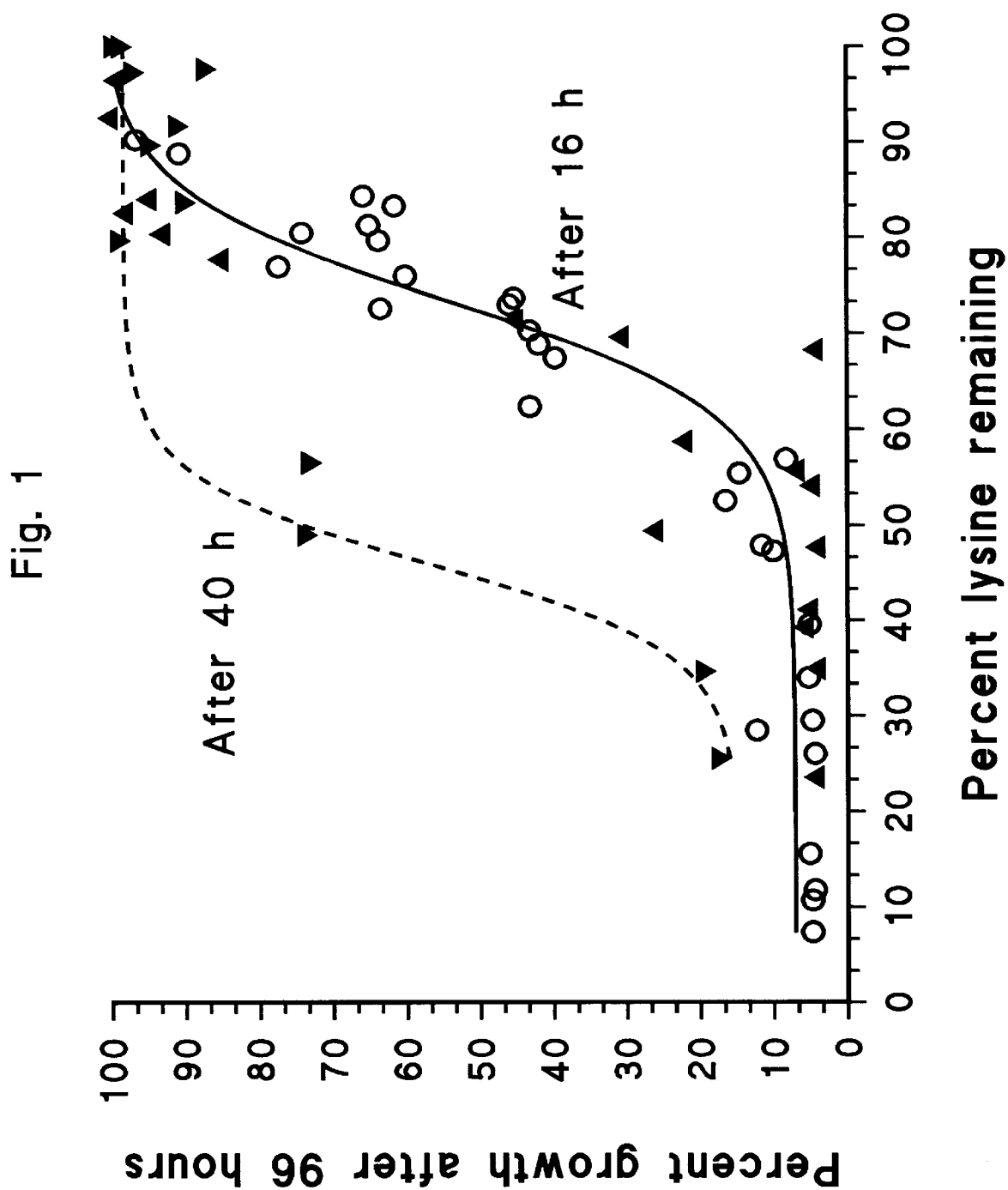
FIG. 1 is a graph showing growth inhibition of HL60 or HeLa cells and lysine depletion by plaque and E. corrodens extracts. In each culture, depletion of lysine was measured from an aliquot of culture fluid after 16 h or 40 h, and inhibition of growth was measured after 96 h. E. corrodens extract, ▲—▲ after 16 h and ▼—▼ after 40 h. Plaque extract, ○ . . . ○ after 16 h.

About 82% of E. corrodens species and about 8% of C. gingivalis and C. ochracea species have lysine decarboxylase on their cell surface [27]. It is contemplated herein that during gingivitis healthy sulci become infected with E. corrodens, C. gingivalis and C. ochracea which deplete the interstitial fluid transudate of the amino acid lysine. The turnover of coronal DAT cells required to maintain the epithelial attachment is thereby inhibited and the resulting irritated attachment attracts neutrophils and the inflammatory exudate (crevicular fluid). Proteins and nutrients in this fluid, but absent from the interstitial fluid, enable the disease-associated bacteria to grow, colonize the sulcus and maintain disease by making short chain fatty acids [1].

Accordingly, the present invention contemplates that inhibitors of lysine decarboxylase slow the rate at which the crevicular fluid, the disease-associated flora, and gingivitis reestablish following tooth debridement and therapy. These inhibitors are agents that reduce the activity of lysine decarboxylase in plaque, or prevent its production by the bacteria in plaque. Although lysine decarboxylase is not found in mammalian cells, lysine may be decarboxylated by ornithine decarboxylase during polyamine synthesis, the product (cadaverine) being exported into the culture medium [28]. Because polyamine synthesis is associated with cell division [29], the additional loss of lysine in this way makes DAT cell turnover and maintenance of the tooth attachment uniquely susceptible to lysine depletion. Thus, preventing lysine depletion before the disease-associated flora develops is contemplated herein to be a useful new method for controlling or inhibiting the re-development of periodontal disease following therapy and as a prophylactic treatment to prevent or inhibit initial gingivitis and periodontitis.

The present invention therefore, is a method of preventing, inhibiting or treating gingivitis by inhibiting the action of lysine decarboxylase in the periodontal region. The method uses an inhibitor of lysine decarboxylase in an oral dosage form such as a tablet, mouthwash, toothpaste, adhesive paste, or periodontal packet. The inhibitor may alternatively be applied intravenously. The invention further comprises a composition comprising a lysine decarboxylase inhibitor, disposed in an oral dosage form such as a tablet, capsule, powder, mouthwash, adhesive paste, or any other oral dosage form known to one of ordinary skill in the art. For example, the composition may further comprise any one of many toothpastes or adhesive pastes, known to those of ordinary skill in the art wherein a lysine decarboxylase inhibitor is added thereto in an effective concentration for inhibiting lysine decarboxylase. The invention also comprises a periodontal packet for oral use. In any of the above embodiments of the invention, the inhibitor may be encapsulated in a coating for providing a slow-release action in a manner well known to one of ordinary skill in the art.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

Toxins are often a principal virulence factor in microbial disease [30]. The use of various mammalian cell cultures has permitted the toxic and growth-inhibiting effects of bacterial plaque to be studied under defined and reproducible conditions [20]. HeLa cells were originally used as the primary target because they are of epithelial origin like DAT cells. However, HL60 cells were used later because they are precursors of neutrophils [31] whose function appears important in controlling the development of periodontitis in response to the bacterial flora [32]. These cells are faster growing than HeLa cells and more sensitive to growth inhibition [22]. Short-chain carboxylic acids, primarily butyrate and propionate, account for less than 15% of the growth-inhibiting activity of plaque extracts to mammalian cell cultures. Proteins account for the remaining activity [21].

Severe periodontitis (attachment loss in young adults) is associated with deficient neutrophil functions and, in localized juvenile periodontitis, also with a predominance of *Actinobacillus actinomycetemcomitans* (Aa) leukotoxin, a protein that exclusively lyses macrophages and promyelocytes, such as HL60 cells and neutrophils [33]. However, the leukotoxic strains of Aa are normally absent from sulci in adult periodontitis [12] and HL60 target cells are growth-inhibited rather than lysed by the toxic proteins from bacterial plaque. The bacterial plaque-derived agents that inhibit cell growth do not have the biological activity of Aa leukotoxin associated with juvenile periodontitis.

Monoclonal antibodies (mabs), from plaque extract-immunized mice, neutralize much of the growth inhibitory effect of plaque on target cells [23]. These mabs detect antigens in *E. corrodens, Actinomyces odontolyticus* and certain viridans streptococci such as *Streptococcus mitis* [23,34]. The fraction of bacteria that bears these antigens was detected by the plaque toxin-neutralizing mabs and found to increase from 0.5% to 4.5% of the flora as a measure of gingival inflammation at the sampled site correspondingly increased. In other words, the more severe the gingivitis, the greater the fraction of antigen-bearing bacteria at the sulcus [34]. Saline extracts of mab-reactive *E. corrodens* but not *S. mitis* inhibit the growth of mammalian cells in culture. The appearance of HL60 cells after treatment with the *E. corrodens* extracts is shown in [24].

Similar effects are observed with HeLa target cells. Unlike *E. corrodens* extracts that contain a number of mab-reactive antigens, the non-toxic *S. mitis* extracts contain a single mab-reactive antigen that is observed on Western immunoblots (140kilodaltons). This antigen was subjected to polyacrylamide gel electrophoresis, cut out and used to make IgG antibodies in rabbits. The IgG antibodies strongly cross-reacted with the largest of the mab-reactive antigens in *E. corrodens* extracts, an 80 kilodalton protein (p80), and also immunoprecipitated it with loss of the toxic activity [24]. Thus, this p80 protein probably mediates the toxic activity of *E. corrodens* extracts [24].

Additional studies describe how p80 was identified to be lysine decarboxylase and responsible for the growth inhibition of target cells. *E. corrodens* cells were grown for 65 h, the cell pellet extracted into saline and subjected to 2-dimensional polyacrylamide gel electrophoresis. The p80 protein was cut out from the gel and digested with LysC protease. Internal peptide sequences were found to be strongly homologous to lysine decarboxylases from enteric bacteria. Using degenerate primers and PCR, a radiolabeled probe was obtained and the complete gene sequence determined from an *E. corrodens* genomic DNA template.

Lysine decarboxylase converts lysine to cadaverine, which was measured calorimetrically. The percent growth of target cells exposed to *E. corrodens* for 96 h was graphed against the percent of lysine remaining in the growth medium (not converted to cadaverine). At doses of extract where there was no growth after 96 h, all the lysine had been converted to cadaverine. When the growth was reduced to 50%, lysine had fallen to 70% of the initial concentration after 16 h and to 45% after 40 h. A virtually identical result was obtained for extracts of bacterial plaque (FIG. 1).

The results of FIG. 1 were obtained when 0.1 ml of *E. corrodens* extract (10 µg protein/ml), or plaque extract (100 µg protein/ml) was added to $0.5 \times 10^5$ HL60 cells or $2 \times 10^5$ HeLa cells in 0.5 ml growth medium in 48-well plates (Costar, Cambridge, Mass.). The cells were incubated for 96 h at 37° C. in 5% $CO_2$ in air, examined visually and counted on a Coulter Counter (Coulter Electronics Hialeah, Fla.). Control HL60 cell cultures contained no extract and increased 10–15-fold in number (100% growth) during the 4 day incubation period [24]. Control HeLa cell cultures increased 8–10 fold. To measure cadaverine, the buffer or culture fluid (142.5 µl) was chilled, precipitated with ice-cold trichloroacetic acid (10% wt/vol) and centrifuged. The supernatant (100 µl) was placed in a large test tube and assayed for cadaverine by the procedure of Phan et al [44]. Samples were diluted to 1.0 ml with sodium acetate (0.5 M, pH 6.0). Potassium carbonate (1 ml of 1.0 M) was added to make the solution alkaline, followed immediately by trinitrobenzenesulfonic acid (TNBS, 1 ml of 0.3% w/v). The samples were incubated at 43° C. for 5.0 min, vortexed with 2.0 ml toluene for 20 sec, centrifuged at 2,000 rpm for 5 min and the absorbance of the toluene layer read at 340 nm. From a standard curve, the cadaverine produced was measured and subtracted from the amount of free lysine initially in the medium plus extract after 16 h or 40 h. The percent lysine remaining was calculated and graphed against percent growth after 96 h. Fig P, a computer program (Fig P Software Corp., Durham, N.C.) provided logit curve-fits ($r^2$) that were all >0.99.

A 15 amino acid sequence at the putative active site of the encoded *E. corrodens* enzyme was synthesized as an octameric, multiple antigenic peptide (MAP) and used to immunize a goat. Immune but not pre-immune goat IgG antibodies prevented both growth inhibition and lysine depletion by *E. corrodens* extracts (FIGS. 2A–B).

To obtain the results in FIGS. 2A–2B, the IgG antibodies from immune and pre-immune goats were purified by precipitation with sodium sulfate, passed through a DE52 cellulose column [24], concentrated to 5 mg/ml over a YM10 Membrane (Amicon Inc., Beverley, Mass.) and salt-exchanged into PBS pH 7.2. The Millipore Filter sterilized IgG was added to a sterile microfuge tube containing 20 mg of *E. corrodens* protein in 0.2 ml of 65 mM NaCl at a 200-fold excess mass of immune or pre-immune IgG in 0.3 ml of PBS. The mixture was rocked for 40 min at room temperature, centrifuged and 140 ul of each mixture added to 0.8 ml medium in wells containing $0.5 \times 10^5$ HL60 cells. Graphs show the percent growth inhibition after 96 h (2A) and the percent lysine remaining (2B) after 40 h incubation (obtained as described in legend to FIG. 1). Standard deviations of the duplicate measurements were within 10% of the mean (not shown).

Figure 4B:
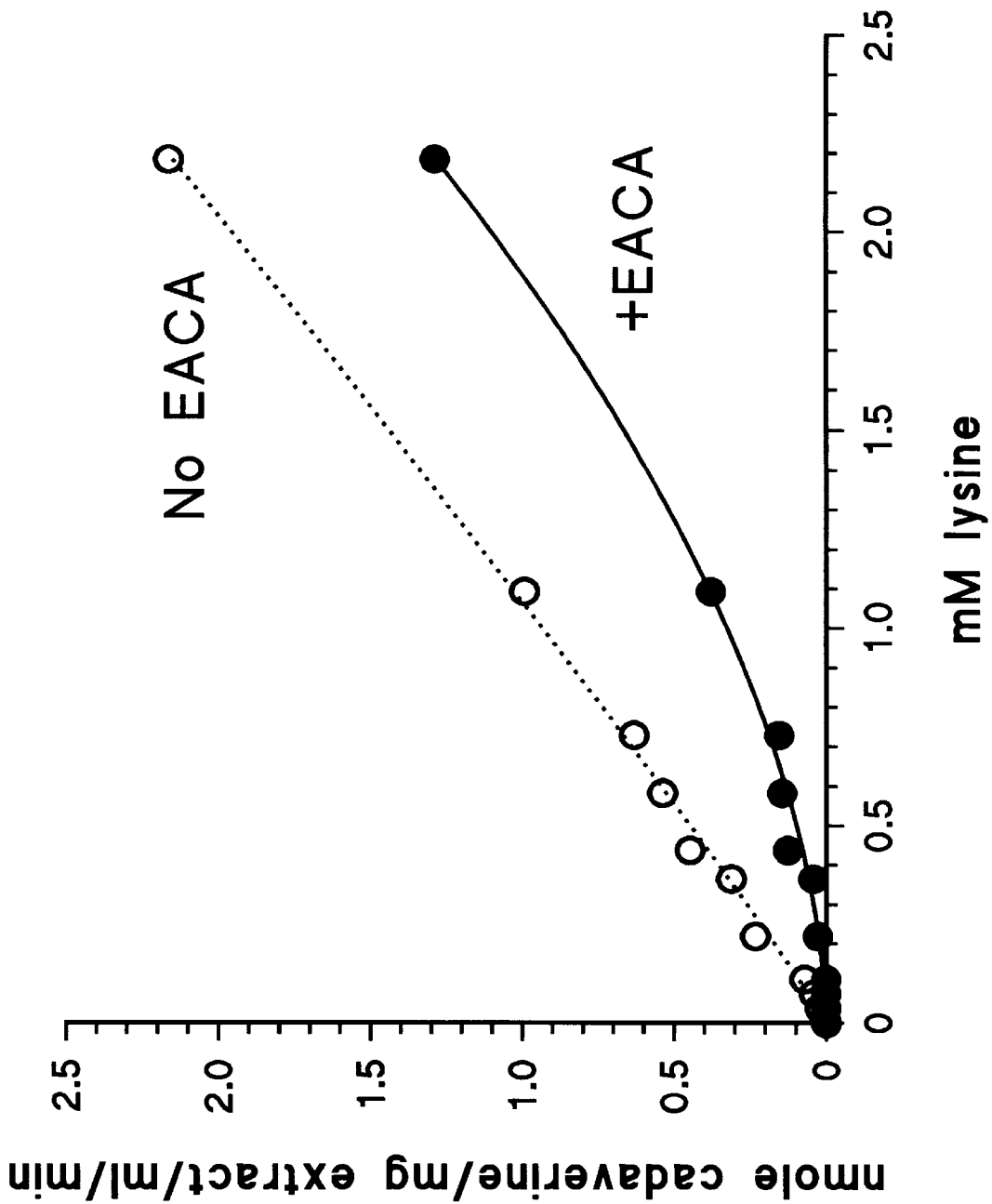

To obtain the results in FIG. 3, extra lysine was added to reduce the rate of lysine depletion and it indeed decreased the growth inhibiting activity of the protein in *E. corrodens* extract (+lysine curve is shifted to the right of the control curve). Conversely, adding ε-amino-n-caproic acid (EACA) increased the growth inhibition (+EACA curve is shifted to the left of the control curve). Adding both lysine and EACA decreased the growth inhibition (+lysine/+EACA curve is shifted to the right of the control curve) but less than lysine alone (curve not as far to the right as the +lysine curve). FIG. 4A and B is provided to show that, for the *E. corrodens* enzyme, EACA indeed activates the enzyme at the low concentrations used in growth media (0.22–0.72 mM), although it inhibits the enzyme at high lysine concentrations as reported previously for the *E. coli* enzyme [26].

Example 2

As noted above, lysine decarboxylase converts lysine to cadaverine in the interstitial fluid and this inhibits DAT cell proliferation during the initial bacterial colonization of the sulcus. This enzyme therefore induces the crevicular fluid flow and promotes the colonization by disease-associated bacteria which maintain the injury to the DAT and surrounding cells by making short chain carboxylic acids. The continued presence of short chain fatty acids from the disease-associated flora is generally believed to constitute the primary bacterial mediator of periodontal disease [14].

Initial development of the disease-associated flora in the absence of oral hygiene should be retarded and the subjects should be protected from periodontal disease when low molecular weight inhibitors which abolish the expression or activity of lysine decarboxylase are exposed to the interstitial fluid of healthy gingival sulci.

The α-halogenomethyl analogues of DL-α-amino acids are enzyme-activated, irreversible inhibitors of the parent α-amino acid decarboxylases. In one embodiment of the present invention, DL-α-difluoromethyl-lysine (DFML, CAS4 699SS-47-1) was synthesized [35]. Concentrations ranging from about 0.1 to about 1mM were found to completely inhibit lysine decarboxylase activity in *Mycoplasma dispar* [36] and *Selenomonas ruminantium* [37]. The corresponding analogues of ornithine and arginine (DFMO and DFMR) had no effect on lysine decarboxylase activity in either of these studies.

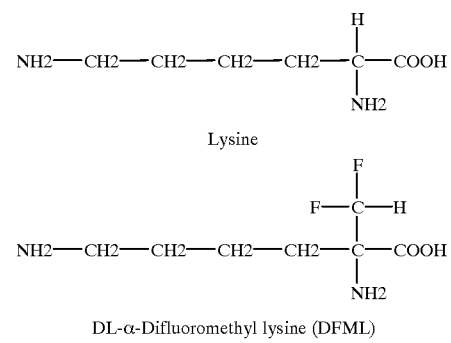

Lysine

DL-α-Difluoromethyl lysine (DFML)

Lysine DL-α-Difluoromethyl lysine (DFML)

In DFML, the hydrogen attached to the alpha-carbon atom of lysine is substituted with a carbon atom having a hydrogen and two fluorine atoms. Methods of synthesis of DFML and of other halomethylated alpha-amino acids are described in [35], which is hereby incorporated by reference in its entirety). DFML has been used for retarding tumor growth, treating psoriasis, and for treating benign prostate hypertrophy.

The mechanism of action of DFML follows the formation of a Schiff base between the free amino group and pyridoxal phosphate on the enzyme. The Schiff base undergoes decarboxylation and loss of the fluoride atoms, leaving a highly reactive Michael acceptor which can be alkylated by a nucleophilic residue in or near the active site to irreversibly bind the enzyme [35].

DFML has been referred to as a suicide inhibitor. It is apparent that the enzyme should only bind to L-DFML and, therefore, that the content of inhibitor included in formulations need only be half the inhibiting values for the DL-form. For example, for inhibiting values of 0.1 to 1.0 mM, (23 to 230 mg DL-DFML/1) the equivalent L inhibitory values would be 0.05–0.50 mM of L-DFML (11.5–115.0 mg L-DFML/1).

In a preferred embodiment, DL-DFML or L-DFML can be orally administered. Examples of preparations that use DFML as a treatment for periodontal disease are A) tablets, B) solutions for injection, C) mouthwashes or irrigation solutions and D) toothpastes, and E) a periodontal adhesive for post-therapeutic local management. In an alternative embodiment the inhibitor may be DL- or L-α-monofluoromethyl lysine (MFML).

Formulations of Preferred Embodiments

Tablets: A preferred dry oral dosage form (e.g., tablet, capsule, powder) comprises 1–2 g of L-DFML. However, doses of as little as 10 mg or as much as 5.0 g are contemplated. A typical tablet might have 0.1 to 2 g of DFML mixed with 0.2 g of starch as a binder. Details of tablet design and formulation are given in Ref. [41] and are well known to those of ordinary skill in the art.

In an intravenous injection, 1 ml of 0.01–1.0 M L-DFML (between 2.30 and 230 mg) in 1 ml physiological saline would be given, for example, one to several times per day.

An irrigation solution or mouthwash would preferably comprise 1–1000 mM of L-DFML. For example, an initially suggested dose would be 0.1 M, (i.e., 200 times the dose of L-DFML that inhibits the enzyme from *Mycoplasma dispar* [36] or *Selenomonas ruminantium* [37]). DFML could, for example, be added to mouthwashes noted in reference [42] in a manner well understood by those of ordinary skill in the art.

A toothpaste would preferably comprise 1–1000 mM L-DFML (similar to the mouthwash). DFML could be added to toothpastes noted in reference [43] in a manner well understood by those of ordinary skill in the art.

An adhesive paste in one embodiment, is ORABASE from Colgate modified so that each gram contains from 1–1000 mg of L-DFML (0.01–10.0%). The paste vehicle may comprise, for example, pectin, gelatin, sodium carboxymethyl-cellulose dispersed in a plasticized hydrocarbon gel composed of 5% polyethylene in mineral oil and flavored with imitation vanilla. Other types of adhesive pastes or teeth coatings will readily occur to those of ordinary skill in the art.

All references cited herein are hereby incorporated herein in their entirety by reference.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

REFERENCES

1. Offenbacher S. (1996) Periodontal Diseases: Pathogenesis. Annals Periodontol. 1, 821–878.
2. Haffajee A. D. & Socransky S. S. (1994) Microbial etiological agents of destructive periodontal diseases. Periodontol. 2000 5, 78–111.
3. Haffajee A. D., Cugini M. A., Dibart S., Smith C., Kent R. L. J. & Socransky S. S. (1997) The effect of SRP on the clinical and microbiological parameters of periodontal diseases. J. Clin. Periodontol. 24, 324–334.
4. Dzink J. L., Socransky S. S. & Haffajee A. D. (1988) The predominant cultivable microbiota of active and inactive lesions of destructive periodontal diseases. J. Clin. Periodontal. 15, 316–323.
5. Haffajee A. D., Dzink J. L. & Socransky S. S. (1988) Effect of modified Widman flap surgery and systemic tetracycline on the subgingival microbiota of periodontal lesions. J. Clin. Periodontal. 15, 255–262.
6. Haffajee A. D., Cugini M. A., Dibart S., Smith C., Kent Jr. R. L. & Socransky S. S. (1997) Clinical and microbiological features of subjects with adult periodontitis who responded poorly to scaling and root planing. J. Clin. Periodontol. 24, 767–776.
7. Ciancio S. G. (1986) Current status of indices of gingivitis. J. Clin. Periodontol. 13, 375–378.
8. Loesche W. J. & Syed S. A. (1978) Bacteriology of human experimental gingivitis: effect of plaque and gingivitis score. Infect. Immun. 21, 830–839.
9. Kolenbrander P. E. (1993) Coaggregation of human oral bacteria: potential role in the accretion of dental plaque. J. Appl. Bacteriol. 74 (Symp. Suppl.), 79S–86S.
10. Kolenbrander P. E., Ganeshkumar N., Cassels F. J. & Hughes C. V. (1993) Coaggregation: specific adherence among human oral plaque bacteria. FASEB J. 7, 406–413.
11. Moore W. E. C., Holdeman L. V., Smibert R.M., Good I. J., Burmeister J. A., Palcanis K. G. & Ranney R. R. (1982) Bacteriology of experimental gingivitis in young adult humans. Infect. Immun. 38, 651–657.
12. Socransky S. S., Haffajee A. D., Cugini M. A., Smith C. & Kent R. L. J. (1998) Microbial complexes in subgingival plaque. J. Clin. Periodontol. 25, 134–144.
13. Niederman R., Buyle-Bodin Y., Lu B.-Y., Robinson P. & Naleway C. (1997) Short-chain carboxylic acid concentration in human gingival crevicular fluid. J. Dent. Res. 76, 575–579.
14. Niederman R., Zhang J. & Kashket S. (1997) Short-chain carboxylic-acid-stimulated, PMN-mediated gingival inflammation. Crit. Rev. Oral Biol. Med. 8, 269–290.
15. Williams R. C. (1990) Periodontal disease. New Eng. J. Med. 322, 373–382.
16. Salonen J. I. (1994) Proliferative potential of the attached cells of human junctional epithelium. J. Periodont. Res. 29, 41–45.
17. Griffiths G. S., Wilton J. M. A. & Curtis M. A. (1997) Permeability of the gingival tissues to IgM during an experimental gingivitis study in man. Arch. Oral Biol. 42, 129–136.
18. Schroeder H. E. & Listgarten M. A. (1977) *Fine structure of the developing epithelial attachment of human teeth, Vol. 2.* S.Karger, Basel.
19. Overman D. O. & Salonen J. I. (1994) Characterization of the human junctional epithelial cells directly attached to the tooth (DAT cells) in periodontal disease. J. Dent. Res. 73, 1818–1823.
20. Levine M., Adams R. L. P. & Cowley G. C. (1973) Effect of dental plaque extracts on mammalian cells in vitro. J. Periodont. Res. 8, 296–303.
21. Levine M. (1985) The role for butyrate and propionate in mediating HeLa-cells growth inhibition by human dental plaque 20 fluid from adult periodontal disease. Arch. Oral Biol. 30, 155–159.
22. Levine M., Movafagh B. F. & Schwartzott D. L. (1987) Characterization and cross-reactivity of rabbit antisera to plaque toxins. Oral Microbiol. Immunol. 2, 88–91.
23. Levine M. & Miller F. C. (1991) Use of monoclonal antibodies with neutralizing effects on toxic antigens from human bacterial plaque to detect specific bacteria by colony blotting. J. Clin. Microbiol. 29, 2809–2816.
24. Levine M. & Miller F. C. (1996) An Eikenella corrodens toxin detected by plaque toxin-neutralizing monoclonal antibodies. Infect. Immun. 64, 1672–1678.
25. Levine M. & Liang Z. (1998) Lysine decarboxylase—a new virulence factor in gingivitis. J. Dent. Res. 77, 110. (Abstract)
26. Sabo D. L., Boeker E., Byers B., Waron H. & Fischer E. H. (1974) Purification and physical properties of inducible *Escherichia coli* lysine decarboxylase. Biochemistry 13, 662–670.
27. Holmes B., Pickett M. J. & Hollis D. G. (1995) Unusual Gram-negative bacteria, including *Capnocytophaga. Eikenella. Pasteurella, and Streptobacillus*. In: *Manual of clinical microbiology* (Edited by Murray P. R.) pp. 499–508. ASM Publications, Washington D.C.
28. Hawel III L., Tjandrawinata R., Fukumoto G. H. & Byus C. V. (1994) Biosynthesis and selective export of 1,5-diaminopentane (cadaverine) in mycoplasma-free cultured mammalian cells. J. Biol. Chem. 269, 7412–7418.
29. Janne J., Poso H. & Raina A. (1978) Polyamines in rapid growth and cancer. Biochim. Biophys. Acta 473, 241–293.
30. Finlay B. B. & Falkow S. (1989) Common themes in microbial pathogenicity. Microbial. Rev. 53, 210–230.
31. Simpson D. L., Berthold P. & Taichman N. S. (1988) Killing of human myelomonocytic leukemia and lymphocytic cell lines by *Actinobacillus actinomycetemcomitans*. Infect. Immun. 56, 1162–1166.
32. Genco R. J., Van Dyke T. E., Levine M. J., Nelson R. D. & Wilson M. E. (1986) Molecular factors influencing neutrophil defects in periodontal disease. J. Dent. Res. 65, 1379–1391.
33. Lally E. T., Golub E, Kieba I. R., Taichman N. S., Rosenbloon J., Rosenbloom J. C., Gibson C. W. & Demuth D. R. (1989) Analysis of the *Actinobacillus actinomycetemcomitans* leukotoxin gene: delineation of unique features and comparison to homologous toxins. J. Biol. Chem. 264, 15451–13564.
34. McAnally J. R. & Levine M. (1993) Bacteria reactive to plaque-toxin-neutralizing monoclonal antibodies are related to the severity of gingivitis at the sampled site. Oral Microbiol. Immunol. 8, 69–74.
35. Bey P., Vevert J-P., Van Dorsselaer V. & Kolb M. (1979) Direct synthesis of alpha-hologenomethyl-alpha-amino acids from the parent alpha-amino acids. J. Org. Chem. 44, 2732–2742.
36. Poso H., McCann P. P., Tanskanen R., Bey P. & Sjoerdsma A. (1984) Inhibition of growth of *Mycoplasma dispar* by DL-alpha-difluoromethllysine, a selective irreversible inhibitor of lysine decarboxylase, and reversal by cadaverine (1,5-diamainopentane). Biochem. Biophys. Res. Comm. 125, 205–210.
37. Kamio Y., Poso H., Terawaki Y. & Paulin L. (1986) Cadaverine covalently linked to a peptidoglycan is an essential constituent of the peptidoglycan necessary for the normal growth in *Selenomonas ruminantium*. J. Biol. Chem. 261, 6585–6589.
38. Pegg A. E. & McGill S. (1979) Decarboxylation of ornithine and lysine in rat tissues. Biochim. Biophys. Acta 568, 416–427.
39. Rudnic E. M. & Kattke M. K. (1996) Tablet dosage forms. In: *Modern Pharmaceutics, Third edition revised and expanded* (Edited by Banker G. S. & Rhodes C. T.) pp. 333–394. Marcel Dekker, Inc., N.Y.
40. Nairn J. G. (1999) Solutions, emulsions, suspensions and extracts. In: *Remington's Pharmaceutical Sciences* (Edited by Hoover J. E.) pp. 1519–1544. Mack Printing Co., Easton, Pa.
41. Ciancio S. G. & Bourgault P. C. (1989) *Clinical pharmacology for dental professionals*. pp. 405–407. Year Book Medical Publishers Inc., Chicago.
42. Phan, A. P. H., Ngo, T. T. & Lenhoff., H. M. 1982. Spectrophotometric assay for lysine decarboxylase. Anal. Biochem. 120:193–197.

What is claimed:

1. A method of treating or preventing gingivitis or periodontitis in a patient whose oral flora includes plaque bacteria producing lysine decarboxylase to prevent or inhibit lysine decarboxylase activity, as a prophylactic treatment to prevent or inhibit initial gingivitis or periodontitis or in patients afflicted with gingivitis or periodontitis for controlling or inhibiting the redevelopment of gingivitis or periodontitis, comprising:

providing a composition comprising an inhibitor of lysirie decarboxylase in a pharmaceutically acceptable carrier or vehicle; and exposing the composition to at least a portion of the periodontal region of the mouth of the patient.

2. The method of claim 1 wherein the inhibitor of lysine decarboxylase is $\alpha$-difluoromethyl lysine or $\alpha$-monofluoromethyl lysine.

3. The method of claim 2 wherein the $\alpha$-difluoromethyl lysine or $\alpha$-monofluoromethyl lysine is L-$\alpha$-difluoromethyl lysine and L-$\alpha$-monofluoromethyl lysine, respectively.

4. The method of claim 1 wherein the pharmaceutically acceptable carrier or vehicle is selected from the group consisting of a tablet, a capsule, a powder, a periodontal packet, a mouthwash, an irrigation solution, a toothpaste, or an adhesive paste, gel or solution for forming a film or coating on the teeth of the patient.

5. A method of treating gingivitis or periodontitis in a patient whose oral flora includes plaque bacteria producing lysine decarboxylase to prevent or inhibit lysine decarboxylase activity, as a prophylactic treatment to prevent or inhibit initial gingivitis or periodontitis or in patients afflicted with gingivitis or periodontitis for controlling or inhibiting the redevelopment of gingivitis or periodonititis, comprising intravenously administering a composition comprising a lysine decarboxylase inhibitor disposed within a pharmaceutically acceptable carrier or vehicle.

6. The method of claim 5 wherein the lysine decarboxylase inhibitor is $\alpha$-difluoromethyl lysine or $\alpha$-monofluoromethyl lysine.

7. The method of claim 6 wherein the $\alpha$-difluoromethyl lysine or $\alpha$-monofluoromethyl lysine is lysine is L $\alpha$-difluoromethyl lysine and L$\alpha$-monofluoromethyl lysine, respectively.

8. The method of claim 5 wherein the pharmaceutically acceptable carrier or vehicle is a saline solution.

* * * * *

UNITED STATES PATENT AND TRADEMARK OFFICE
CERTIFICATE OF CORRECTION

PATENT NO. : 6,103,220
DATED : August 15, 2000
INVENTOR(S) : Martin Levine

It is certified that error appears in the above-identified patent and that said Letters Patent is hereby corrected as shown below:

Column 1,
Line 13, under the Subtitle: STATEMENT REGARDING FEDERALLY SPONSORED RESEARCH OR DEVELOPMENT, delete the words ·not applicable" and substitute therefor the following: -- The research was supported in part by Grant No. DE 11186. The U.S. Government has certain rights in this invention".

Column 10,
Lines 21 and 47, delete the word "plague" and substitute therefor the word -- plaque --.
Line 28, delete the word "lysirie" and substitute therefore the word -- lysine --.
Line 60, after the capital letter "L" at the end of the sentence, add a hyphen.
Line 61, after the capital letter "L" in the middle of the line, add a hyphen.

Signed and Sealed this

Twelfth Day of March, 2002

Attest:

Attesting Officer

JAMES E. ROGAN
Director of the United States Patent and Trademark Office